(12) United States Patent
Chen et al.

(10) Patent No.: US 10,251,568 B2
(45) Date of Patent: Apr. 9, 2019

(54) METHOD AND SYSTEM FOR OPTICAL BLOOD PRESSURE MONITORING

(71) Applicant: Agency for Science, Technology and Research, Singapore (SG)

(72) Inventors: Zhihao Chen, Singapore (SG); Soon Huat Ng, Singapore (SG); Ju Teng Teo, Singapore (SG); Xiufeng Yang, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1091 days.

(21) Appl. No.: 14/372,631

(22) PCT Filed: Jan. 14, 2013

(86) PCT No.: PCT/SG2013/000018
§ 371 (c)(1),
(2) Date: Jul. 16, 2014

(87) PCT Pub. No.: WO2013/109188
PCT Pub. Date: Jul. 25, 2013

(65) Prior Publication Data
US 2015/0018637 A1 Jan. 15, 2015

(30) Foreign Application Priority Data
Jan. 16, 2012 (SG) ................ 201200333-1

(51) Int. Cl.
*A61B 5/02* (2006.01)
*A61B 5/021* (2006.01)
(Continued)

(52) U.S. Cl.
CPC ........ *A61B 5/02125* (2013.01); *A61B 5/0059* (2013.01); *A61B 5/0295* (2013.01); *A61B 5/1102* (2013.01)

(58) Field of Classification Search
CPC ...... A61B 5/021; A61B 5/0295; A61B 5/1102
See application file for complete search history.

(56) References Cited

U.S. PATENT DOCUMENTS

| | | | | |
|---|---|---|---|---|
| 6,498,652 B1* | 12/2002 | Varshneya | ............. | A61B 5/113 356/477 |
| 2002/0058876 A1* | 5/2002 | Chen | ..................... | A61B 5/021 600/485 |
| 2013/0310700 A1* | 11/2013 | Wiard | ................ | A61B 5/02125 600/485 |

FOREIGN PATENT DOCUMENTS

| | | |
|---|---|---|
| WO | WO-2008/095318 | 8/2008 |
| WO | WO-2012/103296 | 8/2012 |
| WO | WO-2013/109188 | 7/2013 |

OTHER PUBLICATIONS

"Smart Pillow for Heart Rate Monitoring Using A Fiber Optic Sensor" by Chen et al., Proceedings of SPIE, vol. 7894, 2011.*
(Continued)

Primary Examiner — Christian Jang
(74) Attorney, Agent, or Firm — Schwegman Lundberg & Woessner, P.A.

(57) ABSTRACT

An apparatus, methods and a system for cuffless blood pressure monitoring are provided. The system includes an optical BCG sensor, a PPG sensor, a transceiver and a signal processing device. The BCG sensor optically couples to the subject, acquires BCG signals from the subject, and optically transmits the subject's BCG signals. The PPG sensor optically couples to the subject for acquiring PPG signals from the subject and optically transmits the acquired subject's PPG signals. The transceiver is coupled to the BCG sensor and the PPG sensor for receiving the BCG signals and the PPG signals and generating a BCG electronic signal from the subject's BCG signals and a PPG electronic signal from the subject's PPG signals. And the signal processing (Continued)

device is coupled to the transceiver for receiving the BCG electronic signal and the PPG electronic signal and for monitoring the subject's blood pressure in response to predetermined BCG indicia of the BCG electronic signal and predetermined PPG indicia of the PPG electronic signal.

18 Claims, 8 Drawing Sheets

(51) Int. Cl.
    *A61B 5/00* (2006.01)
    *A61B 5/0295* (2006.01)
    *A61B 5/11* (2006.01)

(56) References Cited

OTHER PUBLICATIONS

Pinheiro et al (Blood Pressure and Heart Rate Variabilities Estimation Using Ballistocardiography, 2009, Proc Conf. on Telecommunications—ConfTele, Santa Maria da Feira, Portugal, vol. I, pp. 1-4).*

Espina et al (Wearable Body Sensor Network towards Continuous Cuff-less Blood Pressure Monitoring, 2008, Proceedings of the 5th International Workshop on Wearable and Implantable Body Sensor Networks, in conjunction with The 5th International Summer School and Symposium on Medical Devices and Biosensors, The Chinese University of Hong Kong, HKSAR.*

"International Application No. PCT/SG2013/000018, International Search Report dated Mar. 19, 2013", (Mar. 19, 2013), 5 pgs.

Casanella, R., et al., "On Time Interval Measurements Using BCG", 2012 Annual International Conference of the IEEE Engineering in Medicine and Biology Society (EMBC), (2012), 5034-5037.

He, David DA, et al., "The Ear as a Location for Wearable Vital Signs Monitoring", 2010 Annual International Conference of the IEEE Engineering in Medicine and Biology Society (EMBC), (2012), 6389-6392.

Winokur, E. S., et al., "A wearable vital signs monitor at the ear for continuous heart rate and Pulse Transit Time measurements", 2012 Annual International Conference of the IEEE Engineering in Medicine and Biology Society (EMBC), (2012), 2724-2727.

* cited by examiner

US 10,251,568 B2

METHOD AND SYSTEM FOR OPTICAL BLOOD PRESSURE MONITORING

PRIORITY CLAIM

The present application is a U.S. national stage application filed under 35 U.S.C. § 371 from International Application Serial No. PCT/SG2013/000018, which was filed Jan. 14, 2013, and published as WO 2013/109188 on Jul. 25, 2013, and claims priority to Singapore Patent Application No. 201200333-1, filed 16 Jan., 2012, which applications and publication are incorporated by reference as if reproduced herein and made a part hereof in their entirety, and the benefit of priority of each of which is claimed herein.

FIELD OF THE INVENTION

The present invention generally relates to a system and method for blood pressure monitoring, and more particularly relates to systems and methods for optical blood pressure monitoring.

BACKGROUND OF THE DISCLOSURE

A traditional blood pressure measurement system uses an oscillometric method to determine blood pressures based on the relationship of the external pressure and magnitude of arterial volume pulsations. However, patients are not comfortable during the circumferential squeezing of the arm required for such measurements. For long term blood pressure monitoring, the patients sacrifice quality of life in order to maintain such monitoring. Thus, some new methods of cuffless blood pressure monitoring have been proposed in order to measure patients' blood pressure without sacrificing their quality of life. Yet, conventional monitors or devices used for blood pressure measurement/monitoring is often complicated due to rapid and dynamic variations of an individual's blood pressure. Most cuffless blood pressure measurements are based on photoplethysmographic (PPG) and electrocardiogram (ECG) signals. Pulse transmit time (PTT) and pulse arrival time (PAT) are typically used as parameters to determine the blood pressure based on PPG and ECG signals. In addition, during blood pressure monitoring based on ECG measuring, multiple electrodes are typically required to be attached to a patient's chest to determine a time-dependant component of the ECG waveform characterized by a sharp spike.

Thus, what is needed is system and methods for blood pressure monitoring that do not require cuffing a patient's arm or attaching multiple electrodes to the patient's chest. Furthermore, other desirable features and characteristics will become apparent from the subsequent detailed description and the appended claims, taken in conjunction with the accompanying drawings and this background of the disclosure.

SUMMARY

According to the Detailed Description, an apparatus for cuffless blood pressure monitoring is provided. The apparatus includes a ballistocardiogram (BCG) signal measurement device, a photoplethysmographic (PPG) signal measurement device, and a signal processing device coupled to the BCG signal measurement device and the PPG signal measurement device. The BCG signal measurement device optically detects BCG signals and generates therefrom a BCG electrical signal indicative of the BCG signals detected. The PPG signal measurement device optically detects PPG signals and generates therefrom a PPG electrical signal indicative of the PPG signals detected. And the signal processing device monitors blood pressure in response to predetermined BCG indicia of the BCG electrical signal and predetermined PPG indicia of the PPG electrical signal.

A method for cuffless blood pressure monitoring of a subject is also provided. The method includes the steps of optically detecting the subject's BCG and PPG signals, generating a BCG electrical signal from the detected BCG signals and generating a PPG electrical signal from the detected PPG signals, and monitoring the subject's blood pressure in response to predetermined BCG indicia of the BCG electrical signal and predetermined PPG indicia of the PPG electrical signal.

In accordance with another aspect of the present embodiment, a system for cuffless blood pressure monitoring of a subject is provided. The system includes a BCG sensor, a PPG sensor, a transceiver and a signal processing device. The BCG sensor optically couples to the subject, acquires BCG signals from the subject, and optically transmits the subject's BCG signals. The PPG sensor optically couples to the subject for acquiring PPG signals from the subject and optically transmits the acquired subject's PPG signals. The transceiver is coupled to the BCG sensor and the PPG sensor for receiving the BCG signals and the PPG signals and generating a BCG electronic signal from the subject's BCG signals and a PPG electronic signal from the subject's PPG signals. And the signal processing device is coupled to the transceiver for receiving the BCG electronic signal and the PPG electronic signal and for monitoring the subject's blood pressure in response to predetermined BCG indicia of the BCG electronic signal and predetermined PPG indicia of the PPG electronic signal.

BRIEF DESCRIPTION OF THE DRAWINGS

The accompanying figures, where like reference numerals refer to identical or functionally similar elements throughout the separate views and which together with the detailed description below are incorporated in and form part of the specification, serve to illustrate various embodiments and to explain various principles and advantages in accordance with a present embodiment.

FIG. 7, comprising FIGS. 7A and 7B, graphically depict blood pressure monitoring of a first experimental subject using commercial blood pressure monitoring equipment and the cuff-less blood pressure monitoring system of FIG. 1 in accordance with the present embodiment, wherein

FIG. 8, comprising FIGS. 8A and 8B, graphically depict blood pressure monitoring of a second experimental subject using commercial blood pressure monitoring equipment and the cuff-less blood pressure monitoring system of FIG. 1 in accordance with the present embodiment, wherein

Skilled artisans will appreciate that elements in the figures are illustrated for simplicity and clarity and have not necessarily been depicted to scale. For example, the dimensions of some of the elements in the block diagrams may be exaggerated in respect to other elements to help to improve understanding of the present embodiments.

DETAILED DESCRIPTION

The following detailed description is merely exemplary in nature and is not intended to limit the invention or the application and uses of the invention. Furthermore, there is no intention to be bound by any theory presented in the preceding background of the invention or the following detailed description. It is the intent of this invention to present a new cuffless, non-constrained fiber optic blood pressure measurement system based on ballistocardiogram (BCG) signals and photoplethysmographic (PPG) signals from a measured subject.

The system for cuffless blood pressure monitoring in accordance with a present embodiment includes a fiber optic sensing device for optically acquiring BCG signals from a measured subject's back or head or other parts of the body, an optical PPG sensing device for acquiring PPG signals from the measured subject's finger, a transceiver for emitting light signals to the sensing devices and receiving sensing signals from them, and a signal processing unit for filtering noises and calculating the blood pressure of the measured subject. In accordance with this system, the BCG sensing device is a contactless fiber optic sensor. Also, in accordance with the present embodiment, the blood pressure can be monitored and measured without requiring cuffing of the subject's arm or other limb for the blood pressure measurement.

Figure 1:
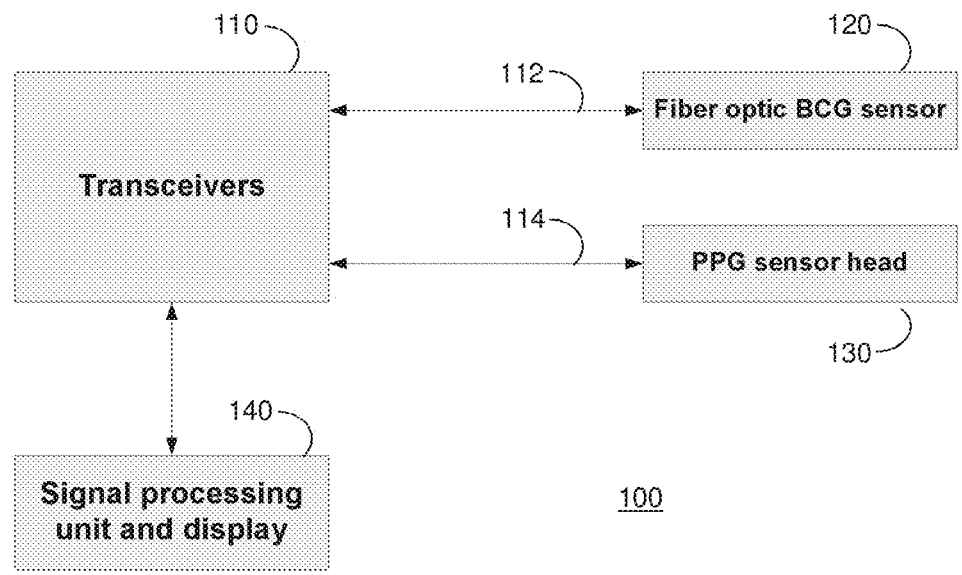
FIG. 1 depicts a block diagram illustrating an overview of a cuffless blood pressure monitoring system in accordance with an embodiment.

Referring to FIG. 1, a block diagram illustrates a cuffless blood pressure monitoring system 100 in accordance with a present embodiment. A transceiver 110 includes optical generation means (as discussed below) and sends optical signals on optical paths 112, 114 respectively to a fiber optic BCG sensor 120, such as a fiber wirebend optic sensor, and a PPG sensor 130, such as a PPG sensor head. The BCG sensor 120 is coupled to a subject (not shown) and acquires the subject's BCG signals. In a manner known to those skilled in the art, the BCG sensor 120 acquires BCG signals by optically detecting the BCG signals from a measured subject's back or head or other part of the body. The PPG sensor head 130 acquires PPG signals by detecting the signals from, for example, a finger of the subject to which the PPG sensor head is attached.

The transceiver 110 optically receives the BCG and PPG signals on the optical signal paths 112, 114 and generates BCG and PPG electronic signals therefrom. The transceiver 110 is electronically coupled to a signal processing unit and display 140. The transceiver 110 provides the BCG and PPG electronic signals to the signal processing unit and display 140 for a signal processing device thereof to monitoring the subject's blood pressure in response to predetermined BCG indicia of the BCG electronic signal and predetermined PPG indicia of the PPG electronic signal. A user interface means of the signal processing unit and display 140 allows control of the transceiver 110 (e.g., operational ON and OFF) and presents final results of the blood pressure measurement for user monitoring such as visually displaying graphical and numeric information representative of the subject's blood pressure and, optionally, presenting audio information including audio representation of the monitored subject's blood pressure and/or audio alerts concerning the subject's blood pressure. In accordance with the present embodiment, the signal processing device of the signal processing unit and display 140 determines a time difference (TD) between predetermined BCG indicia and predetermined PPG indicia and uses the TD to predict the subject's blood pressure.

Figure 2:
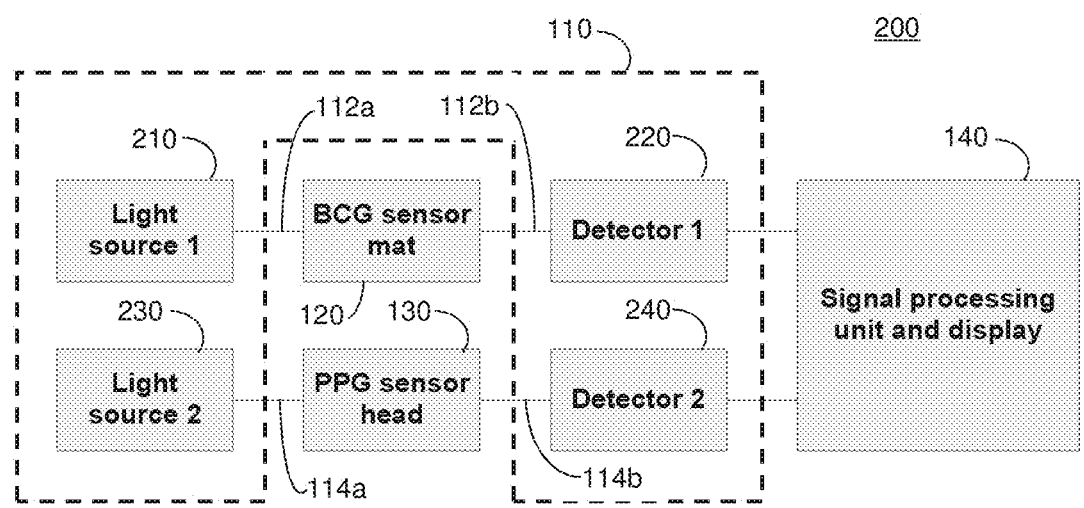
FIG. 2 depicts a block diagram of a dual light source implementation of the cuffless blood pressure monitoring system of FIG. 1 in accordance with the present embodiment.

Referring to FIG. 2, a dual light source system implementation 200 in accordance with the present embodiment is illustrated. A first light source 210 is an optical source which generates light and provides the light along optical path 112a to the BCG sensor 120. The first light source 210 may be a light emitting diode (LED) or a laser and the optical path 112a between the first light source 210 and the BCG sensor 120 can be optical fiber. As described above, the BCG sensor 120 acquires a subject's BCG signal from the subject's head, back or other body part by optical coupling thereto. Optical fiber can also form an optical path 112b from the BCG sensor 120 to a first detector 220 which converts the optical BCG signals into BCG electronic signals.

A second light source 230 is an optical source which provides light to the PPG sensor 130 along an optical path 114a for optically acquiring the subject's PPG signals. The second light source 230 may be a LED or a laser and the optical path 114a could be an optical fiber or just free space. A second detector 240 converts the optical PPG signals into PPG electronic signals. The second light source 230 and the second detector 240 could be co-located with the PPG sensor 130 in the PPG sensor (e.g. in a device coupled to the subject's finger or other phalange) or, as depicted in FIG. 2, parts of the transceiver 110.

The first detector 220 provides the BCG electronic signals to the signal processing unit and display 140 and the second detector 240 provides the PPG electronic signals to the signal processing unit and display 140. The BCG and PPG electronic signals are processed and analyzed in a signal processing device of the processing unit and display 140. The signal processing device may also include filters to filter noise from the first and second detectors 220, 240 and includes peak and valley searching algorithms to determine the time difference (TD) between predetermined BCG indicia of the BCG electronic signal and predetermined PPG indicia of the PPG electronic signal. The TD is utilized in accordance with the present embodiment to predict the subject's blood pressure because the TD is determined such that it is linearly related to the subject's blood pressure and, thus, can advantageously be used continuous, noninvasive and cuffless blood pressure monitoring.

Figure 3:
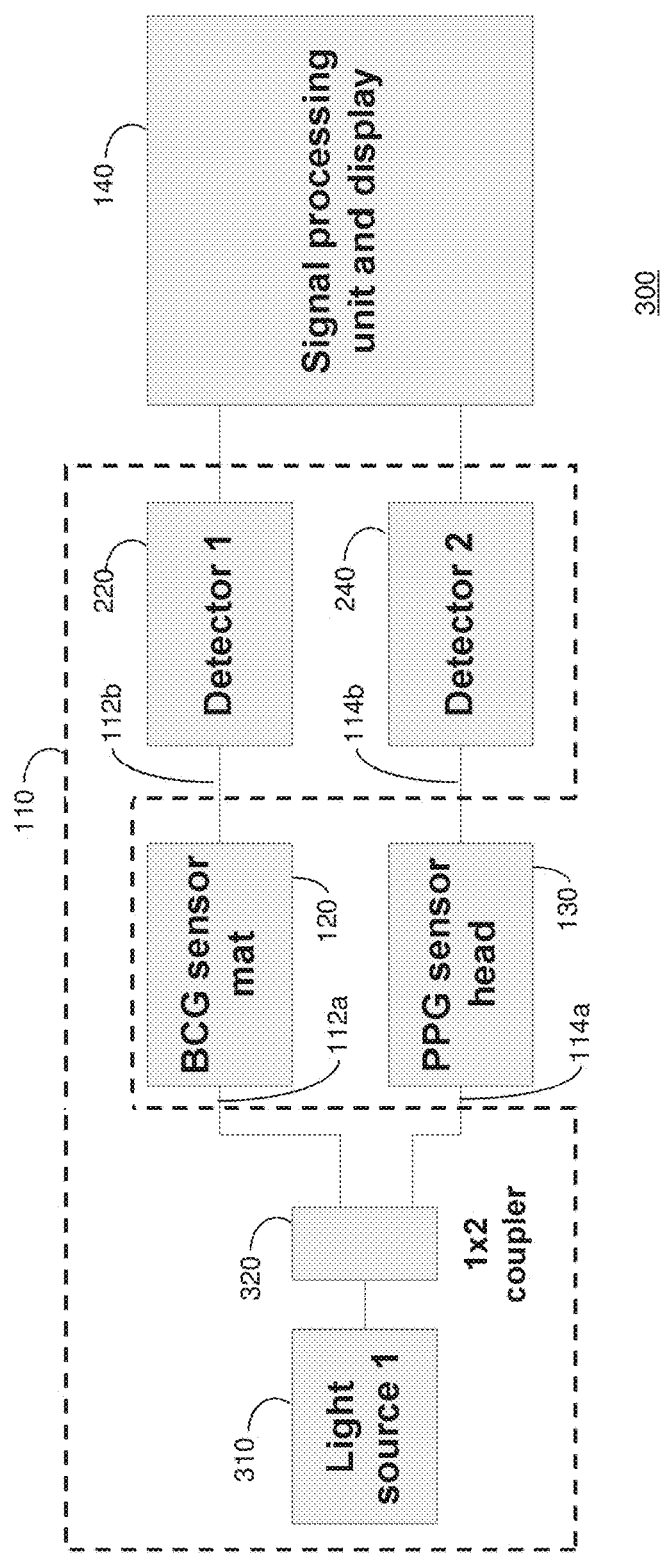
FIG. 3 depicts a block diagram of a single light source implementation of the cuffless blood pressure monitoring system of FIG. 1 in accordance with the present embodiment.

FIG. 3 is a block diagram illustrating a single light source implementation 300 of the cuffless blood pressure monitoring system in accordance with the present embodiment. In the implementation 300, light from an optical source 310 is split into the two optical paths 112a, 114a through an optical coupler 320, such as a 1×2 fiber coupler, for input to the BCG sensor 120 and the PPG sensor 130. In all other respects, implementation 300 uses similar components and operates similarly to implementation 200 (FIG. 2). Thus it can be seen that either the single light source (the optical source 310) or the dual light source (first optical source 210 and second optical source 220) can be used as optical generation means in accordance with the present embodiment. Also, the BCG sensor 120 and the first detector 220 can be considered a BCG signal generation device which acquires and generates the BCG electronic signals. Similarly, the PPG sensor 130 and the second detector 240 can be considered a PPG signal generation device which acquires and generates the PPG electronic signals.

Figure 4:
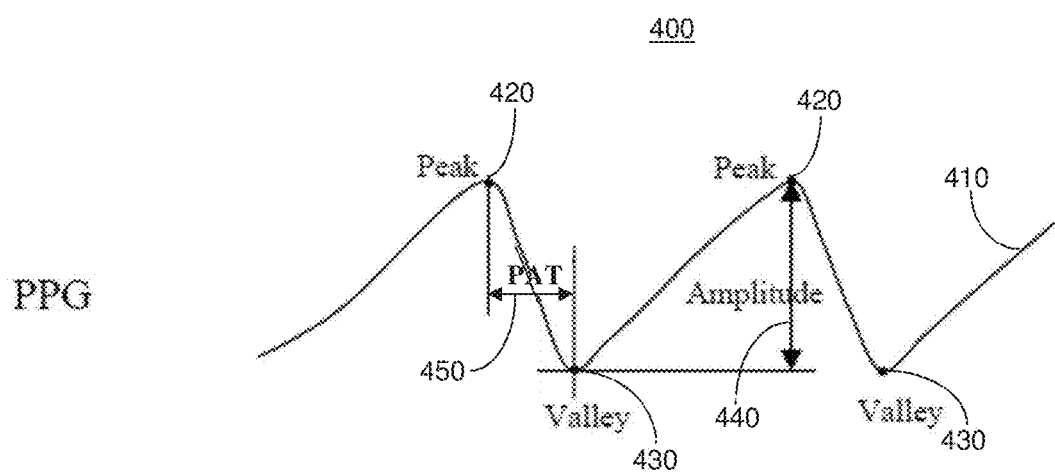
FIG. 4 graphically depicts conventional blood pressure monitoring by computing a pulse arrival time (PAT) using a photoplethysmographic (PPG) waveform.

Referring to FIG. 4, a graphical representation 400 of a conventional monitored PPG electronic signal 410. As seen in the graph 400, the PPG electronic signal 410 includes peaks 420 and valleys 430 with a measurable amplitude 440 between the peaks 420 and the valleys 430. The amplitude 440 and a pulse arrival time (PAT) 450 are used in conventional methodologies to obtain blood pressure measurements from the PPG electronic signal 410. The PAT 450 is the time difference between a peak 420 and a valley 430.

Figure 5:
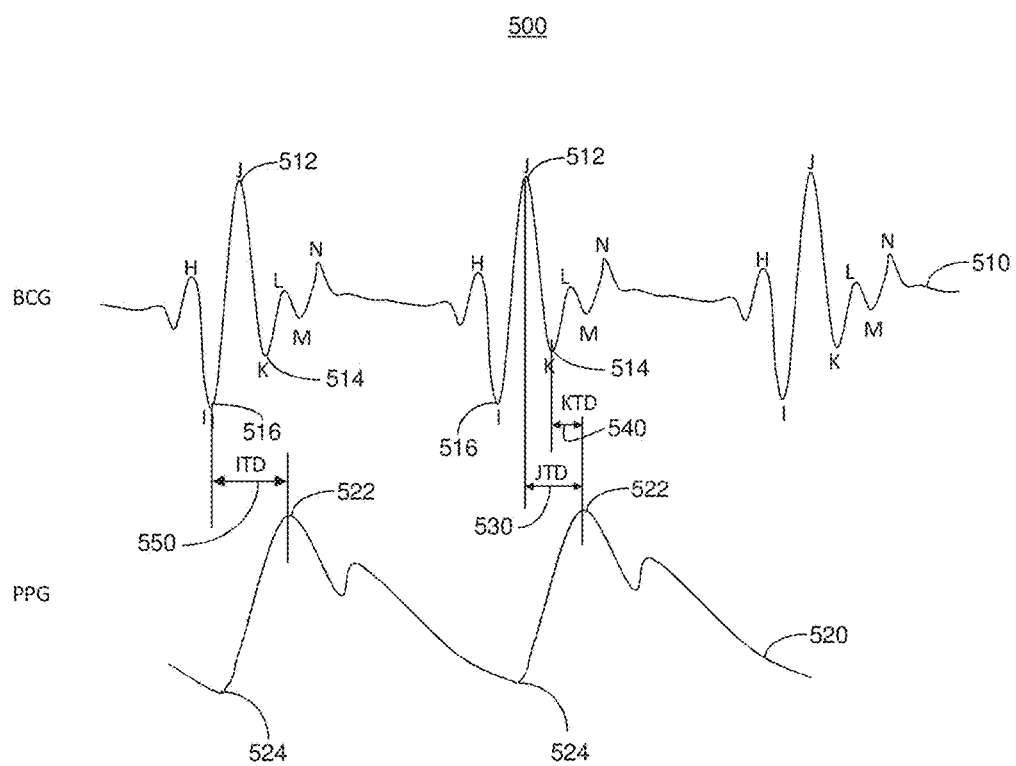
FIG. 5 pictorially depicts monitoring blood pressure by computing a time difference using a ballistocardiogram (BCG) waveform and a photoplethysmographic (PPG) waveform in accordance with the present embodiment.

Referring to FIG. 5, a graphical waveform representation 500 of monitored BCG electronic signal 510 and monitored PPG electronic signal 520 in accordance with the present embodiment is depicted. The signal processing unit and display 140 (FIGS. 1 to 3) is used to detect BCG peak locations (times) and BCG valley locations (times) on the BCG waveform 510 and detect PPG peak locations (times) 522 and PPG valley locations (times) 524 on the PPG waveform 520. The signal processing unit and display 140 then computes the TD by using the BCG waveform 510 and the PPG waveform 520. JTD 530 is the time difference interval between the J-wave 512 of the BCG waveform 510 and a PPG main peak 522 (or valley 524) of the PPG waveform 520. KTD 540 is the interval between the K-wave 514 of the BCG waveform 510 and a PPG main peak 522 (or a PPG valley 524) of the PPG waveform 520. ITD 550 is the interval between the I-wave 516 of the BCG waveform 510 and a PPG main peak 522 (or a PPG valley 524) of the PPG waveform 520.

In accordance with the present invention, predetermined indicia of the BCG waveform 510 (e.g., the J-wave 512, the K-wave 514 or the I-wave 516) and predetermined indicia of the PPG waveform (e.g., a PPG main peak 522 or a PPG valley 524) are utilized to estimate blood pressure. The blood pressure measurement could be determined by using a linear regression method. Thus, the JTD 530, the KTD 540 or the ITD 550 could be used as an indirect measure of blood pressure change, BP=a*JTD+b, for example.

Figure 6:
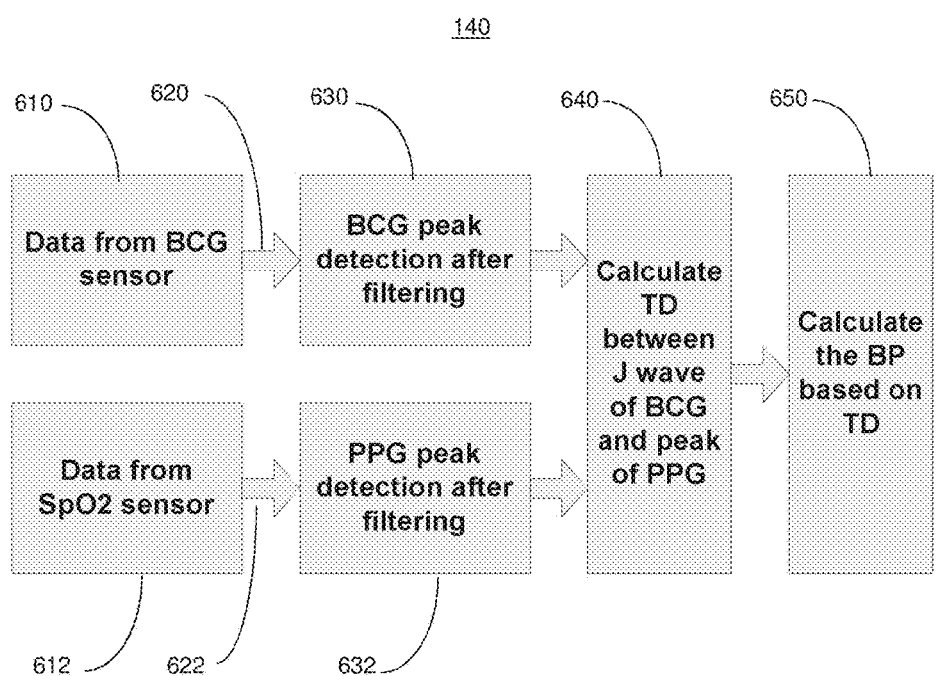
FIG. 6 depicts a block diagram of operational components of the signal processing unit of the cuffless blood pressure monitoring system of FIG. 1 in accordance with the present embodiment.

Referring to FIG. 6, calculation of the main algorithm for blood pressure extraction by the signal processing unit and display 140 is depicted in block diagram form. Data 610 from the BCG sensor 120 is received from the detector 220 (FIGS. 2, 3). In accordance with features of the BCG signals, a band pass filter 620 in the range of two to thirty Hertz is used to filter the BCG signals and a moving average is applied to the BCG signals to smooth them. A BCG peak detection algorithm 630 is then used to extract a J peak 512 (or K or I peak (514, 516)) location from within the BCG signal.

Similarly, data 612 from the PPG sensor 130 is received from the detector 240 (FIGS. 2, 3) and is filtered by a band pass filter 622 in the range of in the range of 0.2 to ten Hertz (as determined by the features of the PPG signal) and smoothed in accordance with a moving average thereof. The location of a peak 522 of the PPG signal is detected by a PPG peak detection algorithm 632.

Based on the information of peak locations of the BCG and PPG signals from algorithms 630, 632, the time delay (JTD) is calculated 640 between a J peak 512 of the BCG signal and a corresponding peak 522 of PPG signal. Then the systolic blood pressure and diastolic blood pressure are estimated 650 based on the time delay (TD) parameter via a linear regression analysis in the form of $$SYS = aTD + b \tag{1}$$

$$DIA = cTD + d \tag{2}$$

where SYS is the systolic blood pressure, DIA is the diastolic blood pressure, and a, b, c, d are calibration constants. The pulse rate could also be estimated from the intervals between PPG peaks 522.

Because the relationship of BCG, PPG and blood pressures are complicated by optical, biomechanical, and physiologic factors, the final calibration constants utilized by the calculation device 650 should be in the form of $$SYS = (a + \Delta a)TD + (b + \Delta b) \tag{3}$$

$$DIA = (c + \Delta c)TD + (d + \Delta d) \tag{4}$$

where $\Delta a$, $\Delta b$, $\Delta c$, and $\Delta d$ are correction factors for each calibration constant a, b, c, and d. These correction factors can easily be obtained by measuring two patient data points from low to high blood pressures under actual measurement/monitoring conditions.

Figure 7A:
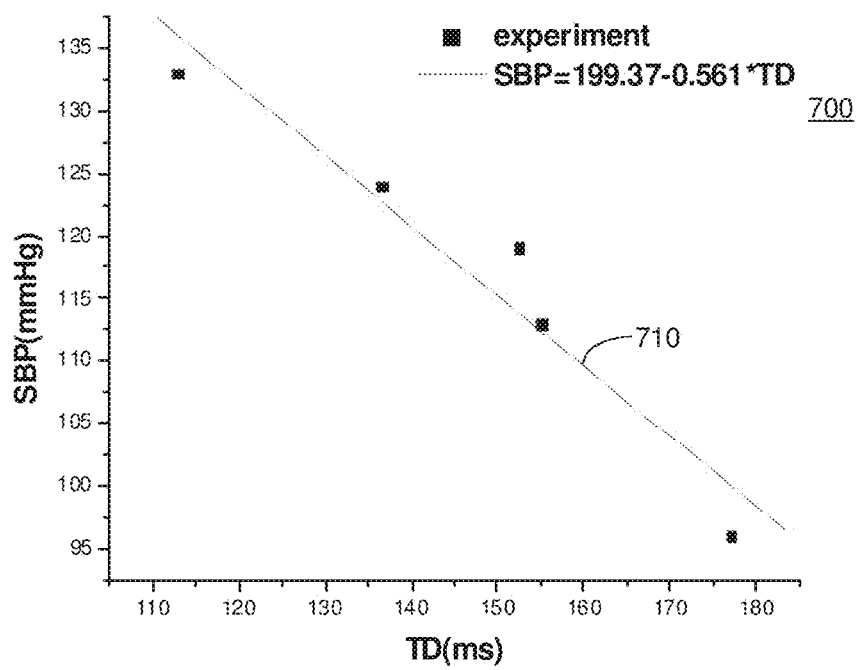
FIG. 7A is a graph of linear regression lines of systolic blood pressure vs. time difference
Figure 7B:
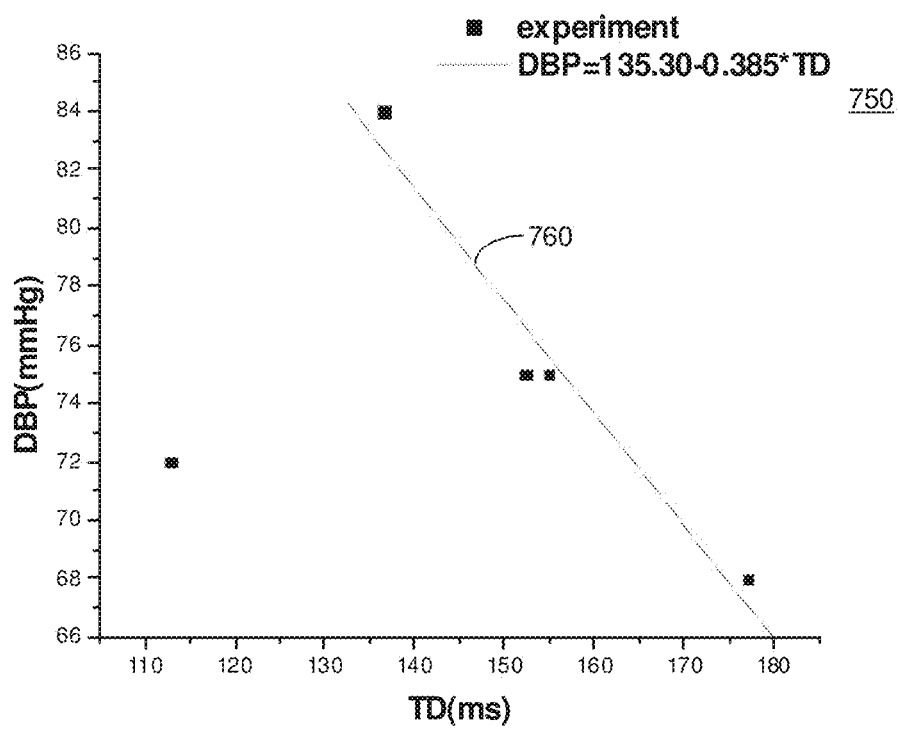
FIG. 7B is a graph of linear regression lines of diastolic blood pressure vs. time difference.
Figure 8A:
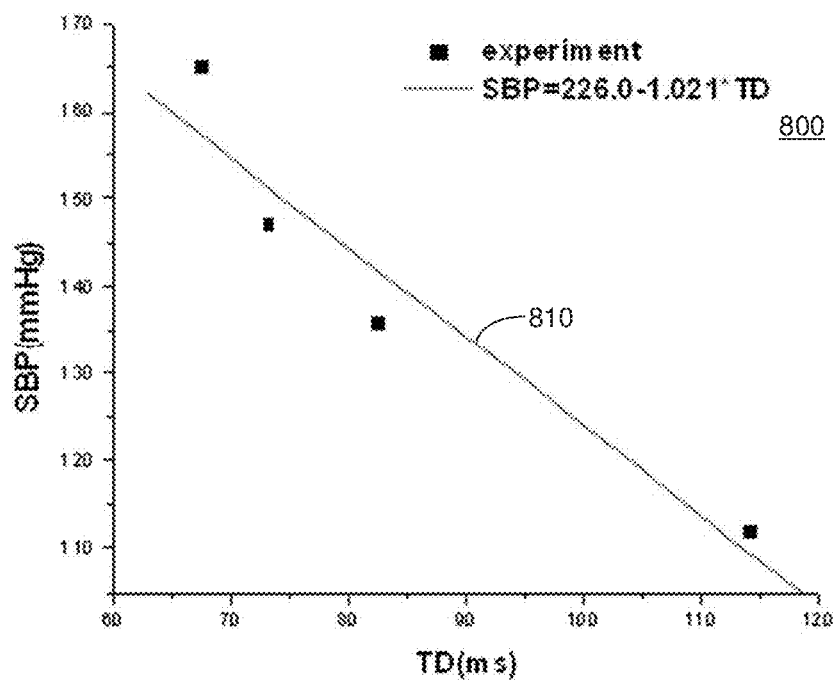
FIG. 8A is a graph of linear regression lines of systolic blood pressure vs. time difference
Figure 8B:
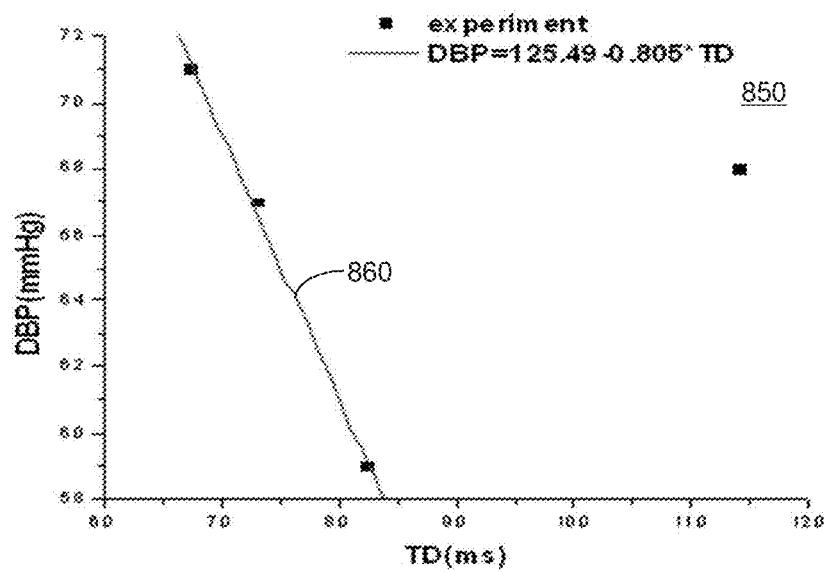
FIG. 8B is a graph of linear regression lines of diastolic blood pressure vs. time difference.

The cuffless BP measurement system 100, 200, 300 includes the PPG sensor head 130 and a microbend fiber sensor 120 to optically acquire the PPG signal and the BCG signal. In accordance with the present embodiment, the PPG signal is acquired from the subject's finger and the BCG signal is acquired from subject's back or head. Referring to FIGS. 7 and 8, experimental results for a first subject 700, 750 and a second subject 800, 850 are shown. FIGS. 7A and 8A depict graphs 700, 800 of linear regression lines 710, 810 of measured systolic blood pressure (SBP) versus calculated TD for the two subjects. The PPG and BCG signals were recorded simultaneously for sixty seconds and used to generate the TD. FIGS. 7B and 8B depict graphs 750, 850 of linear regression lines 760, 860 of measured diastolic blood pressure (DBP) versus the TD for the two subjects to obtain calibration constants. Each measurement point ("■" on the graphs 700, 750, 800, 850) represents the SBP and the DBP measured at the times the TD was calculated. A commercial digital oscillometric blood pressure meter was used to obtain the SBP and DBP reference values and for calibration, and the volunteers were healthy with the blood pressure at the various measurement points regulated by exercises.

Thus it can be seen that the calculated TD is correlated with both SBP and DBP. It was also found that the accuracy of using TD for blood pressure measurement vs. measured SBP and DBP is better than 5% (with one bad measurement point neglected for the DBP comparisons (see FIGS. 7 and 8)).

Figure 9:
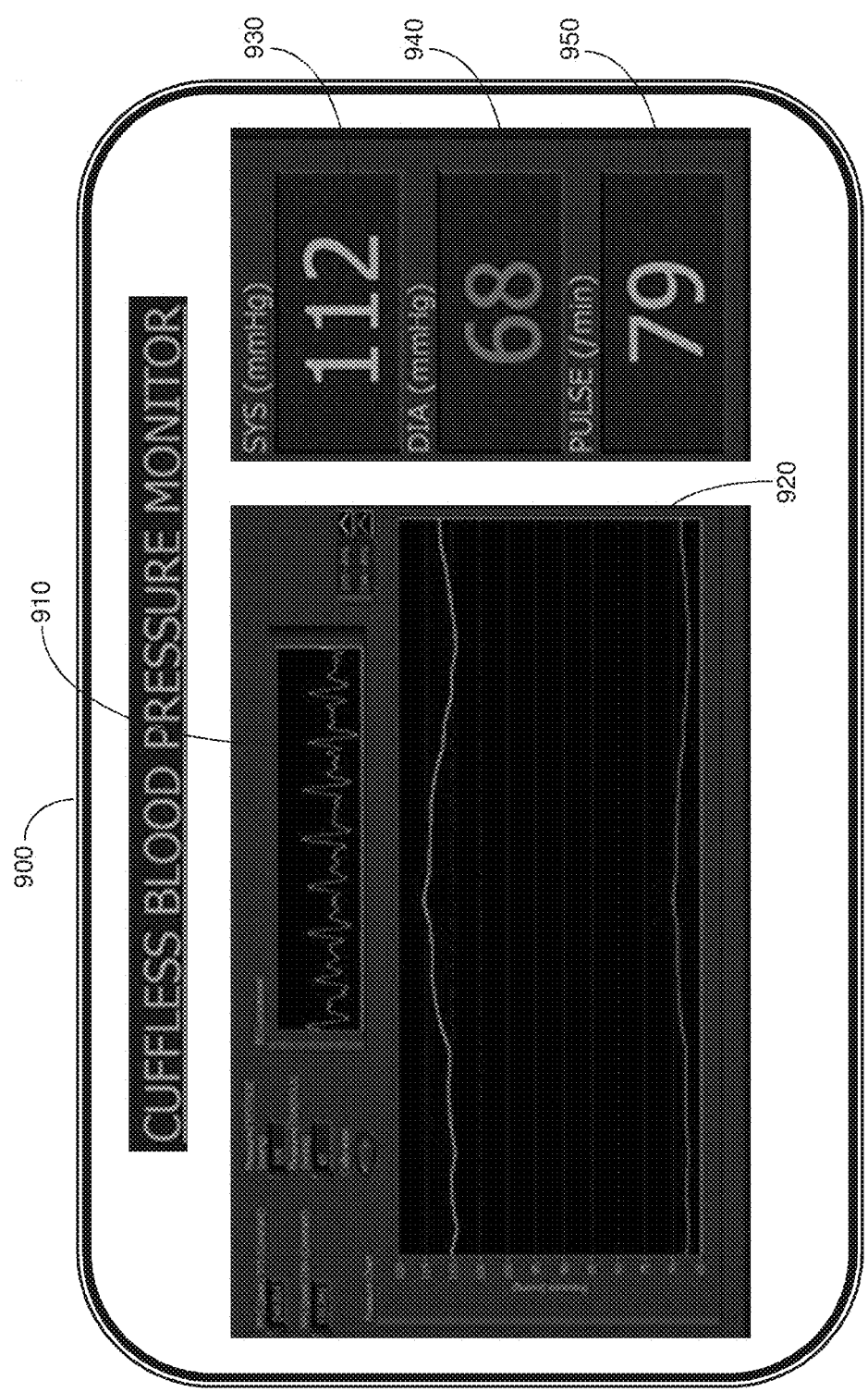
FIG. 9 depicts an example of a user interface of the cuffless blood pressure monitoring system of FIG. 1 in accordance with the present embodiment.

Referring to FIG. 9, a user interface 900 of the cuffless blood pressure monitoring system 100, 200, 300 in accordance with the present embodiment. The user interface 900 would be a display part of the signal processing unit and display 140. The user interface 900 includes graphical visual presentation means such as graphical user interfaces (GUI) 910, 920 for graphically presenting information to a user of the system 100, 200, 300 of a subject's measured blood pressure for monitoring by the user. The user interface 900 also includes numeric visual presentation means such as numeric displays 930, 940, 950 for presenting numeric information to the user of the subject's blood pressure and other measurable parameters (e.g., pulse) for monitoring. While not shown in FIG. 9, the user interface 900 may also include audio presentation means for alerting the user to blood pressure changes (e.g., BP falling below or above designated lower and upper threshold BP measurements) and/or for tracking body parameters such as pulse.

Thus, it can be seen that an all optical method and system to determine both systolic and diastolic blood pressure based on PPG signals from a subject's finger and BCG signals from a subject's back or head has been provided. The all optical system can be used in a magnetic resonance imaging (MRI) room and, thus, provides a MRI safe blood pressure monitoring system. The measurement system of the system in accordance with the present embodiment includes a microbend fiber BCG sensor 120 and an optical PPG sensor 130 for acquiring BCG and PPG signals. While linear regression calculations have been discussed herein, the time difference, JTD 530, KTD 540 or ITD, determined from the PPG signals and the BCG signals may be used to calculate the blood pressures via either linear or nonlinear regression methods. While exemplary embodiments have been presented in the foregoing detailed description of the invention, it should be appreciated that a vast number of variations exist.

It should further be appreciated that the exemplary embodiments are only examples, and are not intended to limit the scope, applicability, operation, or configuration of the invention in any way. Rather, the foregoing detailed description will provide those skilled in the art with a convenient road map for implementing an exemplary embodiment of the invention, it being understood that various changes may be made in the function and arrangement of elements and method of operation described in an exemplary embodiment without departing from the scope of the invention as set forth in the appended claims.

What is claimed is:

1. An apparatus for cuffless blood pressure monitoring comprising:
   a ballistocardiogram (BCG) signal measurement device for optically detecting BCG signals and generating therefrom a BCG electronic signal indicative of the BCG signals detected;
   a photoplethysmographic (PPG) signal measurement device for optically detecting PPG signals and generating therefrom a PPG electronic signal indicative of the PPG signals detected;
   a signal processing device coupled to the BCG signal measurement device and the PPG signal measurement device for monitoring blood pressure in response to predetermined BCG indicia of the BCG electronic signal and predetermined PPG indicia of the PPG electronic signal; and
   optical generation means coupled to the BCG signal measurement device and coupled to the PPG signal measurement device;
   wherein the optical generation means comprises:
      an optical source, and
      an optical coupler coupled to the optical source and configured to split light from the optical source for providing a first optical signal to the BCG signal measurement device for optically detecting the BCG signals and for providing a second optical signal to the PPG signal measurement device for optically detecting the PPG signals.

2. The apparatus in accordance with claim 1 wherein the BCG signal measurement device comprises a fiber optic device for detecting the BCG signals.

3. The apparatus in accordance with claim 2 wherein the fiber optic device comprises a fiber microbend sensor for acquiring the BCG signals.

4. The apparatus in accordance with claim 1 wherein the signal processing device monitors blood pressure in response to the predetermined BCG indicia, the predetermined BCG indicia comprising an indicia selected from a BCG J-wave, a BCG K-wave and a BCG I-wave.

5. The apparatus in accordance with claim 1 wherein the signal processing device monitors blood pressure in response to the predetermined PPG indicia, the predetermined PPG indicia comprising an indicia selected from a PPG peak and a PPG valley.

6. The apparatus in accordance with claim 1 wherein the signal processing device monitors blood pressure in response to a time difference between the predetermined BCG indicia and the predetermined PPG indicia.

7. The apparatus in accordance with claim 1 further comprising user interface means coupled to the signal processing device for presenting information corresponding to the monitored blood pressure, the user interface means comprising one or more of a graphical visual presentation means for graphically presenting information representative of the monitored blood pressure, a numeric visual presentation means for presenting numeric information corresponding to the monitored blood pressure, and audio presentation means for presenting audio information corresponding to at least a portion of the monitored blood pressure.

8. A method for cuffless blood pressure monitoring of a subject, the method comprising the steps of:
   optically detecting the subject's ballistocardiogram (BCG) signals;
   optically detecting the subject's photoplethysmographic (PPG) signals;
   generating a BCG electronic signal from the detected BCG signals and generating a PPG electronic signal from the detected PPG signals;
   monitoring the subject's blood pressure in response to predetermined BCG indicia of the BCG electronic signal and predetermined PPG indicia of the PPG electronic signal; and
   splitting light from an optical source into a first optical signal for optically detecting the BCG signals and a second optical signal for optically detecting the PPG signals.

9. The method in accordance with claim 8 wherein the step of monitoring the subject's blood pressure comprises monitoring the subject's blood pressure in response to one or more predetermined BCG indicia selected from a BCG J-wave, a BCG K-wave, and a BCG I-wave and one or more predetermined PPG indicia selected from a PPG peak and a PPG valley.

10. The method in accordance with claim 8 wherein the step of monitoring the subject's blood pressure comprises monitoring the subject's blood pressure in response to a time difference between the predetermined BCG indicia and the predetermined PPG indicia.

11. The method in accordance with claim 8 wherein the step of monitoring the subject's blood pressure comprises measuring the subject's blood pressure in response to a time difference between the predetermined BCG indicia and the predetermined PPG indicia and calibration constants selected to generate the systolic and diastolic components of blood pressure.

12. The method in accordance with claim 11 wherein the step of monitoring the subject's blood pressure further comprises measuring the subject's blood pressure in response to correction factors for the calibration constants determined in response to optical, biomechanical, and physiologic factors of the optical detection steps and the subject.

13. The method in accordance with claim 8 further comprising providing optical signals for optically detecting the subject's BCG signals and the subject's PPG signals.

14. The method in accordance with claim 13 wherein the step of providing the optical signals comprises providing first optical signals for optically detecting the BCG signals and providing second optical signals for optically detecting the PPG signals.

15. The method in accordance with claim 8 further comprising presenting information corresponding to the monitored blood pressure, the step of presenting information comprising one or more of graphically presenting information representative of the monitored blood pressure, presenting numeric information corresponding to the monitored blood pressure, and presenting audio information corresponding to at least a portion of the monitored blood pressure.

16. A system for cuffless blood pressure monitoring of a subject comprising:
 a ballistocardiogram (BCG) sensor for optically coupling to the subject and acquiring BCG signals from the subject, the BCG sensor further optically transmitting the subject's BCG signals acquired from the BCG sensor;
 a photoplethysmographic (PPG) sensor for optically coupling to the subject and acquiring PPG signals from the subject, the PPG sensor further optically transmitting the subject's PPG signals acquired from the PPG sensor;
 a transceiver coupled to the BCG sensor and the PPG sensor for receiving the BCG signals and the PPG signals and for generating a BCG electronic signal from the subject's BCG signals and for generating a PPG electronic signal from the subject's PPG signals;
 a signal processing device coupled to the transceiver for receiving the BCG electronic signal and the PPG electronic signal therefrom and for monitoring the subject's blood pressure in response to predetermined BCG indicia of the BCG electronic signal and predetermined PPG indicia of the PPG electronic signal; and
 wherein the transceiver comprises optical generation means coupled to the BCG sensor and the PPG sensor for providing optical signals for the BCG sensor to optically acquire the subject's BCG signals and for the PPG sensor to optically acquire the subject's PPG signals; and
 wherein the optical generation means comprises:
  an optical source, and
  an optical coupler coupled to the optical source and configured to split light from the optical source for providing a first optical signal to the BCG sensor for optically acquiring the subject's BCG signals and for providing a second optical signal to the PPG sensor for optically acquiring the subject's PPG signals.

17. The system in accordance with claim 16 wherein the transceiver comprises:
 a first detector coupled to the BCG sensor for receiving the subject's optical BCG signals and generating therefrom the BCG electronic signals; and
 a second detector coupled to the PPG sensor for receiving the subject's optical PPG signals and generating therefrom the PPG electronic signals.

18. The system in accordance with claim 16 further comprising user interface means coupled to the signal processing device for presenting information corresponding to the subject's monitored blood pressure, the user interface means comprising one or more of a graphical visual presentation means for graphically presenting information representative of the subject's monitored blood pressure, a numeric visual presentation means for presenting numeric information corresponding to the subject's monitored blood pressure, and audio presentation means for presenting audio information corresponding to at least a portion of the subject's monitored blood pressure.

* * * * *